United States Patent [19]

Iwamitsu et al.

[11] Patent Number: 5,095,037
[45] Date of Patent: Mar. 10, 1992

[54] COMBINED ANTI-INFLAMMATORY AGENT

[75] Inventors: Kenichi Iwamitsu, Kobe; Yukio Nakamura, Nara; Masahiro Kawasaki, Kashihara; Yoshio Fukui, Ibaraki, all of Japan

[73] Assignee: Nissho Corporation, Osaka, Japan

[21] Appl. No.: 623,318

[22] Filed: Dec. 6, 1990

[30] Foreign Application Priority Data

Dec. 21, 1989 [JP] Japan .................... 1-334571

[51] Int. Cl.$^5$ .......................... A61K 31/195
[52] U.S. Cl. ................................ 514/561
[58] Field of Search ......................... 514/561

[56] References Cited

U.S. PATENT DOCUMENTS

4,808,576  2/1989  Schultz et al. ................ 514/54

FOREIGN PATENT DOCUMENTS

0243867  12/1988  European Pat. Off. .
WO8807060  9/1988  World Int. Prop. O. .

OTHER PUBLICATIONS

Chem-Abst. 109 (1988)-85940y.
Gotoh et al., in Folia pharmacol. japon, 92, pp. 17-27 (1988).
Miyazaki et al., entitled "Sodium Hyaluronate (SPH)", in Ohyo Yakura, 28 (6), pp. 1123-1135 (1984).
Kaito et al., entitled "Anti-inflamatory action of N-(2-,6-dichlorophenol)-o-amino-phenylacetaic acid ...", in Folia pharmacol Japon, 69, pp. 299-318 (1973).

*Primary Examiner*—Stanley J. Friedman
*Attorney, Agent, or Firm*—Varndell Legal Group

[57] ABSTRACT

A pharmaceutical composition for treating inflammatory diseases, comprising (A) an effective amount of hyaluronic acid or its salt, and (B) an effective amount of an anti-inflammatory agent. The composition exhibits a synergistic therapeutic effect on inflammations and is useful for treating inflammatory diseases, particularly diseases of joint with inflammation.

8 Claims, No Drawings

COMBINED ANTI-INFLAMMATORY AGENT

BACKGROUND OF THE INVENTION

The present invention relates to a combined medicine for the purpose of treating inflammatory diseases and more particularly to a combined medicine useful for treating diseases of a joint with inflammation.

It has been known that hyaluronic acid or its salt is effective to some kinds of arthropathies in clinical and fundamental tests. The theoretical bases are as follows: (1) Hyaluronic acid is one of the main components of joint liquid. In the case of rheumatoid arthritis and osreoarthritis which are included in arthropathy, the hyaluronic acid contained in the joint liquid has a reduced molecular weight and a reduced concentration. (2) As the main pharmacological actions of hyaluronic acid, there are exemplified an action of covering the surface of a cartilage, an inhibitory action on the liberation of proteoglycan, which action is exhibited by the hyaluronic acid migrated into a cartilage matrix, and an improving action on the spinnability of the joint liquid.

However, most of the reported clinical cases wherein hyaluronic acid was applied are osteoarthritis and rheumatoid arthritis and its applicable range is relatively narrow. Further, although symptoms such as pain and stiffness become in serious problem in the treatment of joint diseases, hyaluronic acid does not possess any direct activity of improving such symptoms.

Anti-inflammatory agents are widely used in the clinical treatment of arthropathy. The reason therefor is presumed that many kinds of arthropathies involves inflammation. The reason why nonsteroidal anti-inflammatory agents are especially widely used is presumed that they have strong analgesic activity.

However, when anti-inflammatory agents are administered in a usual clinical method such as oral administration, administration using suppository, subcutaneous or intramuscular administration, side effects such as the inflammation and ulcer of digestive system, and diarrhea tend to develop because the drug reaches its effective concentration not only at a part to be treated but also in tissues of the whole body including blood. Further the development of the side effects is promoted due to the fact that a large amount of dose is required for the treatment because of the distribution of the drug over the whole body and the fact that the administration period is prolonged because most arthropathies are chronic. For the reasons, a sufficient amount of the drug required for the treatment cannot be administered or the administration is obliged to be interrupted, which results in failure of a suitable treatment. Consequently, there are many cases wherein the condition of the disease is worsened.

It is an object of the present invention to provide an inflammation-treating agent, in particular, which is capable of curing inflammation in joint diseases and possesses the activity of improving symptoms such as pain and stiffness.

Another object of the invention is to provide an efficient inflammation-treating agent, in particular, which does not develop any side effect even when a sufficient amount thereof required for the treatment of joint diseases is administered.

These and other objects of the present invention will become apparent from the description hereinafter.

SUMMARY OF THE INVENTION

The present invention provides a pharmaceutical composition for treating inflammatory diseases, comprising (A) an effective amount of hyaluronic acid or its salt, and (B) an effective amount of an anti-inflammatory agent.

DETAILED DESCRIPTION

A combined agent of hyaluronic acid or its salt with an anti-inflammatory agent in accordance with the present invention is an excellent agent for treating joint diseases, which develops the respective merits of both drugs and supresses the respective demerits of both drugs.

Hyaluronic acid and its salts possess anti-inflammatory activity. Examples of the salt of hyaluronic acid include sodium salt, potassium salt, ammonium salt and salts with lower alkyl amines ($C_1$ to $C_5$) The sodium salt is preferred.

In a preferable embodiment of the present invention, hyaluronic acid or its salt is used in the form of a solution wherein it is dissolved in water or an aqueous solvent in such a concentration that the solution shows spinnability. An aqueous solution of hyaluronic acid or its salt which shows suitable spinnability has a viscosity of about 500 to 2,000 cps at 300° C. In the case of sodium hyaluronate having a molecular weight of $8 \times 10^5$, a concentration of not less than 0.5% (w/v %, hereinafter the same), preferably 0.8 to 1.2%, is required to obtain such a suitable spinnability. A lower concentration (lower than 0.5%) is adoptable with increasing molecular weight of sodium hyaluronate and a higher concentration (more than 0.5%) is required with decreasing molecular weight of sodium hyaluronate.

Hyaluronic acid or its salt having a molecular weight within a wide range can be used in the present invention. From the viewpoints of the anti-inflammatory activity and spinnability, the preferred molecular weight ranges from $4 \times 10^5$ to $3 \times 10^6$. When the molecular weight is less than the above range, the anti-inflammatory activity is poor and a suitable spinnability is not obtainable. When the molecular weight is more than the above range, the viscosity of the resulting solution extremely increases and consequently the administration by injection is difficult, which results in the impossibility of practical application to the treatment of arthropathy.

In a preferable embodiment of the present invention, the anti-inflammatory agent, which is preferably in the form of finely divided particles, is dissolved or suspended into a solution of hyaluronic acid or its salt in water or an aqueous solvent. The resulting solution or suspension is preferably adjusted so that the pH value is from 6.0 to 7.0 and the ratio of its osmotic pressure to that of a 0.9% physiological saline solution is from 0.8 to 1.2, yielding a preparation suitable for administration in an articular cavity. Examples of the aqueous solvent include physiological saline solutions, 3 to 5% glucose solutions and 3 to 5% xylitol solutions and phosphate buffer solutions.

Both steroidal anti-inflammatory agents including prednisolone and nonsteroidal anti-inflammatory agents can be used as an anti-inflammatory agent. The nonsteroidal anti-inflammatory agents are preferred.

Preferable examples of the nonsteroidal anti-inflammatory agent are as follows:

I Carboxylic acid anti-inflammatory agent

1. Salicylic acid anti-inflammatory agent
   Salicylic acid
   Aspirin
2. Anthranilic acid anti-inflammatory agent
   Mefenamic acid II Acetic acid anti-inflammatory agent
1. Phenylacetic acid anti-inflammatory agent
   Diclofenac
   Alclofenac
2. Indole anti-inflammatory agent
   Indometacin
3. Heteroarylacetic acid anti-inflammatory agent
   Tolmethin III Propionic acid anti-inflammatory agent
1. Phenyl anti-inflammatory agent
   Ibuprofen
2. Naphthalene anti-inflammatory agent
   Naproxen
3. Tricyclic anti-inflammatory agent
   Pranoprofen IV Pyrazolone anti-inflammatory agent
   Phenylbutazone V Benzthiazine anti-inflammatory agent
   Piroxicam The above-mentioned anti-inflammatory agents include their salts, if any. These anti-inflammatory agents may be used singly or in admixtures thereof.

The preferred anti-inflammatory agents are nonsteroidal acid anti-inflammatory agents represented by the following structure formulas (I) and (II):

$$R^1\text{—CHCOOH} \quad\quad (I)$$
$$|$$
$$R^2$$

wherein $R^1$ is

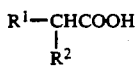 or

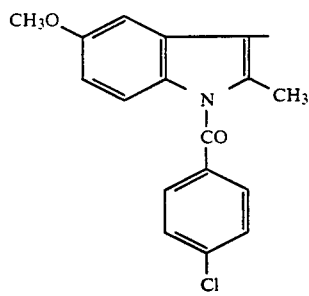

and $R^2$ is —H or —CH$_3$.

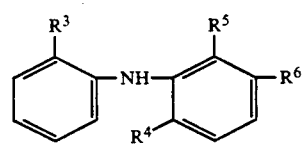 (II)

wherein $R^3$ is —COOH or —CH$_2$COOH, $R^4$ is —H or —Cl, $R^5$ is —Cl or —CH$_3$, and $R^6$ is —H or —CH$_3$.

The more preferred anti-inflammatory agents are shown in Table 1.

TABLE 1

| | R$^1$ | R$^2$ | R$^3$ | R$^4$ | R$^5$ | R$^6$ |
|---|---|---|---|---|---|---|
| 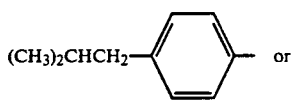 | | —CH$_3$ | —CH$_2$COOH | —Cl | —Cl | —H |
| 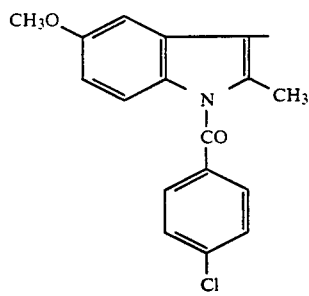 | | —H | —COOH | —H | —CH$_3$ | —CH$_3$ |

In the present invention, the ratio of hyaluronic acid or its salt to the anti-inflammatory agent can vary over a wide range. For the purpose of obtaining a good synergistic effect, the ratio of hyaluronic acid or its salt to the anti-inflammatory agent ranges preferably from 1:0.03 to 2 (by weight), more preferably from 1:0.1 to 1. When the proportion of hyaluronic acid or its salt is lower than the above range, the anti-inflammatory agent is not sufficiently retained by an aqueous solution of hyaluronic acid or its salt. When the proportion of hyaluronic acid or its salt is higher than the above range, the anti-inflammatory activity is lowered.

The combined agent of the present invention may contain other medicaments such as adrenocortical hormones, local anesthetic agents and antibiotics. Further, it may contain various additives including stabilizing agents, for example, antioxidants such as sodium sulfite and sodium hydrogen-sulfite; buffers such as citrates and phosphates; solubilizers or solubilizing agents such as alcohols, polyethylene glycols; and preservatives such as benzoic acid and salicylic acid.

The combined agent of the present invention can be applicable to the treatment of a variety of arthropathies such as osteoarthrisis, rheumatoid arthritis and periarthritis; and gout, and to treatments after operation of joints and eyes.

In the treatment of arthropathy, the combined agent of the present invention is preferably administered into an articular cavity in a dose of 27.5 to 50 mg/one time per adult (based on the total amount of both drugs). More concretely, for example, 2.5 ml ampuls are prepared, each containing 25 mg of sodium hyaluronate and a given amount of an anti-inflammatory agent (e.g. 25 mg of diclofenac, ibuprofen or phenylbutazone, 7.5 mg of indometacin, or 375 mg of sodium salicylate) in an isotonic phosphate buffer solution as an aqueous solvent. The preparation is administered into an articular cavity in a dose of one ampul once per 7 to 10 days. In such a manner, the administration is continuously conducted 4 to 5 times while varying the dose if necessary.

The combined agent of hyaluronic acid or its salt and an anti-inflammatory agent in accordance with the present invention is able to exhibit the effects mentioned below.

The combined agent of the present invention has a wide application as an arthropathy-treating agent because it is composed of two kinds of arthropathy-treating agents different in mechanism of action from each other. The combined agent of the present invention has a strong therapeutic effect due to a synergistic effect of the combination of the two kinds of the components.

The combined agent of the present invention can be administered directly to an affected part to be treated so that the concentration of the drugs becomes higher at the affected part to be treated and lower in tissues, including the tissues of digestive system, other than the tissue to which the instant agent is administered. Thus a strong therapeutic effect is obtained at the affected part and side effects such as ulcer and inflammation of digestive system and diarrhea hardly develop. The interruption of the administration and the extreme reduction of the dose due to the side effects can be avoided. Consequently a sufficient medical treatment is made possible.

Moreover, in the case of the instant combined agent of hyaluronic acid or its salt with an anti-inflammatory agent, the anti-inflammatory agent dissolved in the aqueous solvent is retained in a hydrated hyaluronic acid or its salt for a long time and released gradually therefrom. The effective concentration of the drugs can be retained in the tissue to which the instant combined agent is administered and the action of the drugs continues. Consequently, it is sufficient to administer the instant combined agent about once per a week.

The present invention is more specifically described and explained by means of the following Examples. It is to be understood that the present invention is not limited to the Examples, and various change and modifications may be made in the invention without departing from the spirit and scope thereof.

TEST EXAMPLE 1

The inhibitory effect on carrageenan-induced edema was investigated as to combined agents of sodium hyaluronate (molecular weight: $8 \times 10^5$) and various anti-inflammatory agents.

Wister male rats weighing 240 to 260 g (6 weeks old) were preliminarily bred for not less than 1 week. Eight rats were used in one group. Each test agent shown in Table 2 was dissolved or suspended in an isotonic phosphate buffer solution (pH 7.0) to give a 1% solution or suspension (hereinafter referred to as "1% solution"). The solution was administered subcutaneously into the right foot pad of each rat. Six hours after the administration, a 1% solution of carrageenan was administered subcutaneously as an irritating agent into the right foot pad of the rat in a dose of 0.1 ml/animal. The volume of the right foot pad was measured before and 4 hours after the administration of carrageenan. The rate of edema inhibition (hereinafter referred to as "inhibitory rate") by each test agent was calculated from the obtained measurements and thus the inhibitory effect on edema was evaluated. The results are shown in Table 2.

Table 2 reveals that all anti-inflammatory agents tested, when being used in combination with sodium hyaluronate, showed strong inhibitory effect on edema in comparison with either each anti-inflammatory agent alone or sodium hyaluronate alone. Among the anti-inflammatory agents tested, diclofenac, ibuprofen and indometacin, particularly, showed great synergistic effect in combination with sodium hyaluronate.

The measurement of the volume was carried out according to the method of Fujimura et al. (see Iyakuhin Kaihatsu Kisokoza, Vol. 6, "Yakubutsu no Hyoka (1)" editted by Tsuda and Nogami, p 239–282, Kabushiki Kaisha Chizin-sha, 1971).

The rate of inhibition (%) of the edema of the foot pad of each rat was calculated according to the following formula (III).

$$\text{Inhibitory rate (\%)} = \left(1 - \frac{MTEV}{MCEV}\right) \times 100 \quad \text{(III)}$$

MCEV: Average swollen rate of the foot pad 4 hours after the administration of carrageenan in the control group MTEV: Average swollen rate of the foot pad 4 hours after the administration of carrageenan in the drug-given group $$\text{Swollen rate (\%)} = \frac{(TEV - CEV)}{CEV} \times 100$$

CEV: Volume of foot pad of each rat before the administration of carrageenan

TEV: Volume of foot pad of each rat 4 hours after the administration of carrageenan With respect to each agent, the evaluation of the inhibitory effect on edema was carried out according to the following criteria: Synergistic effect was observed:

| Very great | HA % + DG % ≦ ED % |
|---|---|
| Great | TD % ≦ ED % < HA % + DG % |
| Small | MD % < ED % < TD % |

No synergistic effect was observed:

ED % ≦ MD %

HA %: Inhibitory rate by the administration of sodium hyaluronate alone

DG %: Inhibitory rate by the administration of the anti-inflammatory agent alone ED % : Inhibitory rate by the administration of the combined agent
MD % : {The greater one between HA % and DG %} × 1.2
TD % : HA % + DG % (1—HA %/100)

Besides, the stomach and the small intestine were autopsyed under anesthesia with ether 6 hours after the administration of carrageenan and no abnormal symptom was observed in the drug-given group.

TABLE 2

| Test agent | Dose (mg/kg) | Inhibitory rate (%) | TD % | HA % + DG % | Synergistic effect |
|---|---|---|---|---|---|
| Sodium hyaluronate (HA) | 4.0 | 23.5 | | | |
| Diclofenac sodium | 4.0 | 16.9 | | | |
| HA + Diclofenac sodium | 4.0 + 4.0 | 62.9 | 36.4 | 40.4 | very great |
| Ibuprofen | 4.0 | 18.2 | | | |
| HA + Ibuprofen | 4.0 + 4.0 | 47.6 | 37.4 | 41.7 | very great |
| Sodium salicylate | 50.0 | 46.6 | | | |
| HA + Sodium salicylate | 4.0 + 50.0 | 57.0 | 59.1 | 70.1 | small |
| Indometacin | 1.2 | 12.9 | | | |
| HA + Indometacin | 4.0 + 1.2 | 66.2 | 33.4 | 36.4 | very great |
| Phenylbutazon | 4.0 | 46.1 | | | |
| HA + Phenylbutazon | 4.0 + 4.0 | 59.3 | 58.8 | 69.6 | great |
| Piroxicam | 4.0 | 34.6 | | | |
| HA + Piroxicam | 4.0 + 4.0 | 47.1 | 50.0 | 58.1 | small |
| Prednisolone | 0.5 | 21.7 | | | |
| HA + Prednisolone | 4.0 + 0.5 | 37.0 | 40.1 | 45.2 | small |

Note:
MD % is smaller than ED % with all agents tested.

TEST EXAMPLE 2

The inhibitory effect on carrageenan-induced edema was investigated as to combined agents of various grades of sodium hyaluronates having different molecular weights with diclofenac sodium.

Wister male rats weighing 230 to 265 g (6 weeks old) were preliminarily bred for not less than 1 week. Eight rats were used in one group. A 1% solution of each test agent shown in Table 3 was administered subcutaneously into the right foot pad of each rat. Six hours after the administration, a 1% solution of carrageenan was administered subcutaneously as an irritating agent into the right foot pad of the rat in a dose of 0.1 ml/animal. The volume of the right foot pad was measured before and 4 hours after the administration of carrageenan. Then the inhibitory effect on edema was evaluated in the same way as in Test Example 1. The results are shown in Table 3.

Table 3 reveals that sodium hyaluronates having a molecular weight within a wide range showed synergistic effect in combination with diclofenac sodium. However, sodium hyaluronate having too small molecular weight showed a smaller inhibitory effect itself and therefore the inhibitory effect of the combined agent thereof was also smaller. Accordingly the preferable molecular weight of sodium hyaluronate is not less than $4 \times 10^5$.

TABLE 3

| Test agent | Molecular weight of HA | Dose (mg/kg) | Inhibitory rate (%) |
|---|---|---|---|
| Sodium hyaluronate (HA) | 28 × 10⁴ | 4.0 | −36.4 |
| HA + Diclofenac | 28 × 10⁴ | 4.0 + 4.0 | 19.6 |
| HA | 58 × 10⁴ | 4.0 | 17.9 |
| HA + Diclofenac | 58 × 10⁴ | 4.0 + 4.0 | 38.0 |
| HA | 80 × 10⁴ | 4.0 | 29.9 |
| HA + Diclofenac | 80 × 10⁴ | 4.0 + 4.0 | 49.6 |
| HA | 210 × 10⁴ | 4.0 | 43.2 |
| HA + Diclofenac | 210 × 10⁴ | 4.0 + 4.0 | 52.5 |

TABLE 3-continued

| Test agent | Molecular weight of HA | Dose (mg/kg) | Inhibitory rate (%) |
|---|---|---|---|
| Diclofenac | — | 4.0 | 16.9 |

TEST EXAMPLE 3

The inhibitory effect on carrageenan-induced edema was investigated with respect to combined agents of sodium hyaluronate (molecular weight: $8 \times 10^5$) and diclofenac sodium wherein the ratio of diclofenac sodium to sodium hyaluronate varied.

Wister male rats weighing 235 to 260 g (6 weeks old) were preliminarily bred for not less than 1 week. Eight rats were used in one group. A 1% solution of each test agent shown in Table 4 was administered subcutaneously into the right foot pad of each rat. Six hours after the administration, a 1% solution of carrageenan was administered subcutaneously as an irritating agent into the right foot pad of the rat in a dose of 0.1 ml/animal. The volume of the right foot pad was measured before and 4 hours after the administration of carrageenen. Then, the inhibitory effect on edema was evaluated in the same way as in Test Example 1. The results are shown in Table 4.

As is clear from Table 4, when the ratio of diclofenac sodium to sodium hyaluronate is approximately equal, the preferable results can be expected.

TABLE 4

| Test agent | Dose (mg/kg) | Inhibitory rate (%) |
|---|---|---|
| Sodium hyaluronate (HA) | 4 | 25.9 |
| HA + Diclofenac | 4 + 2 | 29.8 |
| HA + Diclofenac | 4 + 4 | 58.2 |
| HA + Diclofenac | 4 + 8 | 63.9 |

TEST EXAMPLE 4

The inhibitory effect on carrageenan-induced edema was investigated with respect to combined agents of sodium hyaluronate (molecular weight: $8 \times 10^5$) and various acid anti-inflammatory agents.

Wister male rats weighing 240 to 255 (6 weeks old) were preliminarily bred for not less than 1 week. Eight rats were used in one group. A 1% solution of each test agent shown in Table 5 was administered subcutaneously into the right foot pad of each rat. Six hours after the administration, a 1% solution of carrageenen was administered subcutaneously as an irritating agent into the right foot pad of each rat in a dose of 0.1 ml/animal. The volume of the right foot pad was measured before and 4 hours after the administration of carrageenen. Then, the inhibitory effect on edema was evaluated in the same way as in Test Example 1. The results are shown in Table 5.

Table 5 reveals that all anti-inflammatory agents tested, when being used in combination with sodium hyaluronate, showed strong inhibitory effect on edema in comparison with either each anti-inflammatory agent alone or sodium hyaluronate alone.

TABLE 5

| Test agent | Dose (mg/kg) | Inhibitory rate (%) | TD % | HA % + DG % | Synergistic effect |
|---|---|---|---|---|---|
| Sodium hyaluronate (HA) | 4 | 23.9 | | | |
| Aspirin | 4 | 14.6 | | | |
| HA + Aspirin | 4 + 4 | 23.6 | 35.0 | 38.5 | small |
| Mefenamic acid | 4 | 34.2 | | | |
| HA + Mefenamic acid | 4 + 4 | 44.6 | 49.9 | 58.1 | small |
| Alclofenac | 4 | 22.9 | | | |
| HA + Alclofenac | 4 + 4 | 40.4 | 41.3 | 46.8 | small |
| Tolmetin | 4 | 25.1 | | | |
| HA + Tolmetin | 4 + 4 | 42.5 | 43.0 | 49.0 | small |
| Pranoprofen | 4 | 39.0 | | | |
| HA + Pranoprofen | 4 + 4 | 46.8 | 53.6 | 62.9 | small |

TEST EXAMPLE 5

After preliminary breeding of mail ICR mice 5 weeks old weighing 23 to 28 g (5 mice per one group) for one week, a 1% solution of each test agent shown in Table 6 wa subcutaneously administered to the mice. The number of dead mice was counted 72 hours after the administration. The results are shown in Table 6.

The results of Table 6 reveal that the inflammation-testing agents of the present invention have no toxicity.

The doses of the test agent used in this test were about ten times those used in Test Example 1.

TABLE 6

| Test agent | Dose | Number of dead mice |
|---|---|---|
| Sodium hyaluronate (HA) | 40 | 0 |
| HA + Diclofenac sodium | +40 | 0 |
| HA + Sodium salicylate | +500 | 0 |
| HA + Ibuprofen | +40 | 0 |
| HA + Indometacin | +12 | 0 |
| HA + Phenylbutazon | +40 | 0 |
| HA + Piroxicam | +40 | 0 |
| HA + Prednisolone | +5 | 0 |

Note:
The molecular weight of sodium hyaluronate is $8 \times 10^5$. The doses in Table 6 mean the amounts (mg) administered per kg body weight. The dose values, to which the mark "+" is attached, as to the combined agents means the amounts of anti-inflammatory agent added to 40 mg/kg of sodium hyaluronate (HA).

TEST EXAMPLE 6

Wister male rats weighing 240 to 260 g (6 weeks old) were preliminarily bred for not less than 1 week. Eight rats were used in one group. A 1% solution of each test agent shown in Table 7 was administered subcutaneously into the right foot pad of each rat. Sixteen hours after the administration, a 1% solution of carrageenan was administered subcutaneously as an irritating agent into the right foot pad of each rat in a dose of 0.1 ml/animal. The volume of the right foot pad was measured before and 4 hours after the administration of carrageenen. Then, the inhibitory effect on edema was evaluated in the same way as in Test Example 1. The results are shown in Table 7.

As is clear from the results of Table 7, the combined agents composed of indometacin or diclofenac and sodium hyaluronate showed prolonged anti-inflammatory effects even in a low dose which does not cause any side effect. The effects were greater than that in the case of administering sodium hyaluronate alone or that in the case of administering each anti-inflammatory agent alone. Then it would be understood that the synergistic effect of the combined agent of the present invention is very great.

TABLE 7

| Test agent | Dose (mg/kg) | Inhibitory rate (%) | TD % | HA % + DG % | Synergistic effect |
|---|---|---|---|---|---|
| Sodium hyaluronate (HA) | 4.0 | 30.0 | | | |
| Diclofenac | 3.0 | 9.7 | | | |
| HA + Diclofenac | 4.0 + 3.0 | 46.3 | 36.8 | 39.7 | Very great |
| Indometacin | 3.0 | 20 | | | |
| HA + Indometacin | 4.0 + 3.0 | 52.0 | 44.0 | 50.0 | Very great |

TEST EXAMPLE 7

Rabbits (New Zealand White) weighing about 2 kg were preliminarily bred for not less than one week and healthy ones were selected (3 rabbits per group). The joint of right knee of each rabbit was fixed by applying a splint thereto and further completely fixed not so as to move by putting it in plaster. Then the rabbits were bred normally for one month.

During the normal breading, a 1% solution of each test agent shown in Table 8 was administered using an injection needle of gauge No. 27 into the articular cavity of each rabbit except those of the control group in a dose of 0.3 ml/kg body weight once per three days.

One day after the last administration, the splint and the plaster were removed and the movable range of the joint was measured with a protractor under anesthesia with Nembutal (trademark). The rate of inhibition of the damage to the movable range of joint with respect to each test agent was calculated from the obtained measurements and the curative effect was evaluated. The results are shown in Table 8.

In the case of the rabbits of the control group, the adhesion and deformation of the bones were caused in one month normal breeding and a gait disturbance was observed even after removal of the splint and the plaster because the movable range of joint was rendered narrow.

In the case of the rabbits of the drug-given groups, the following is apparent from Table 8. The administration of either diclofenac alone or sodium hyaluronate alone exhibited some curative effect, but the administration of the combined agent of both drugs exhibited an outstanding curative effect That is, the movable range of joint was rendered wider than that of the single drug-given rabbits and the gait disturbance was also outstandingly remedied.

The rate of inhibition of the damage to the movable range of joint was calculated according to the following formula (IV), and the evaluation of synergistic effect was conducted under the same condition as in Test Example 1.

$$\text{Inhibitory rate (\%)} = \frac{(MTJV - MCJV)}{MCJV} \times 100 \quad \text{(IV)}$$

MCJV: Average movable range of joint with respect to the rabbits of the drug-given group
MTJV: Average movable range of joint with respect to the rabbits of the drug-given group

TABLE 8

| Test agent | Dose (mg/kg) | Inhibitory rate (%) | TD % | HA % + DG % | Synergistic effect |
|---|---|---|---|---|---|
| Sodium hyaluronate (HA) | 3.0 | 24.5 | | | |
| Diclofenac | 3.0 | 17.3 | | | |
| HA + Diclofenac | 3.0 + 3.0 | 38.1 | 36.6 | 41.8 | Great |

Molecular weight of sodium hyaluronate: $8 \times 10^5$

PREPARATION EXAMPLE 1

A combined agent having the following formula was prepared.

| | |
|---|---|
| Sodium hyaluronate | 25 mg |
| Diclofenac sodium | 5 mg |
| 4% solution of glucose or 4% solution of xylitol | 2.5 ml |

PREPATATION EXAMPLE 2

Combined agents having following formulas were prepared.

| | |
|---|---|
| Sodium hyaluronate | 25 mg |
| Diclofenac sodium | 5 to 25 mg |
| Sodium hydrogensulfite | 1 to 25 mg |
| 4% solution of glucose or 4% solution of xylitol | 2.5 ml |

In addition to the ingredients used in the Examples, other ingredients can be used in the Examples as set forth in the specification to obtain substantially the same results.

What we claim is:

1. A pharmaceutical composition for treating inflammatory diseases comprising an effective amount of a combination of (A) hyaluronic acid or a salt thereof and (B) a nonsteroidal anti-inflammatory agent for treating inflammatory diseases selected from the group consisting of a compound having formula (I):

wherein $R^1$ is a group selected from the group consisting of groups having formulas (II), (III) and (IV):

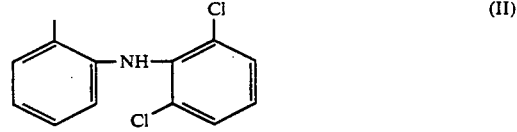

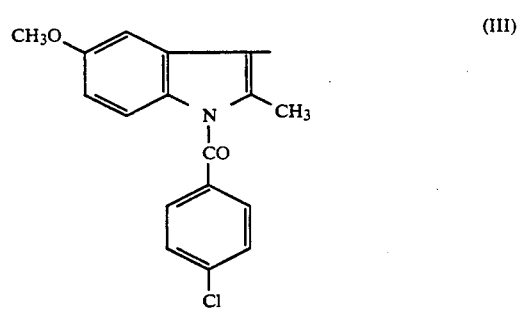

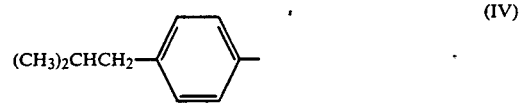

and $R^2$ is H provided that $R^1$ is group II or group III, or $R^2$ is —$CH_3$ provided that $R^1$ is group IV; and a salt thereof.

2. The composition of claim 1, wherein the ingredient (a) is sodium hyaluronate.

3. The composition of claim 1, wherein the nonsteroidal anti-inflammatory agent is an acid anti-inflammatory agent.

4. The composition of claim 1, which is a treating agent for arthropathy.

5. The composition of claim 4, which is in a preparation form suitable for the administration into an articular cavity.

6. The composition of claim 1, wherein the nonsteroidal anti-inflammatory agent is diclofenac.

7. The composition of claim 1, wherein the ingredient (A) has a molecular weight from $4 \times 10^5$ to $3 \times 10^6$.

8. The composition of claim 1, wherein the ingredients (A) and (B) are present in a ratio of the hyaluronic acid or a salt thereof to the anti-inflammatory agent from 1:0.03 to 2 by weight.

* * * * *

REEXAMINATION CERTIFICATE (2752th)

United States Patent [19]

Iwamitsu et al.

[11] B1 5,095,037

[45] Certificate Issued Dec. 19, 1995

[54] COMBINED ANTI-INFLAMMATORY AGENT

[75] Inventors: Kenichi Iwamitsu, Kobe; Yukio Nakamura, Nara; Masahiro Kawasaki, Kashihara; Yoshio Fukui, Ibaraki, all of Japan

[73] Assignee: Nissho Corporation, Osaka, Japan

Reexamination Request:
No. 90/002,988, Mar. 4, 1993

Reexamination Certificate for:
Patent No.: 5,095,037
Issued: Mar. 10, 1992
Appl. No.: 623,318
Filed: Dec. 6, 1990

[30] Foreign Application Priority Data

Dec. 21, 1989 [JP] Japan .................................. 1-334571

[51] Int. Cl.$^6$ ................................................ A61K 31/195
[52] U.S. Cl. ............................................................ 514/561
[58] Field of Search ................................................ 514/561

[56] References Cited

FOREIGN PATENT DOCUMENTS 0197718 10/1986 European Pat. Off. .

OTHER PUBLICATIONS

M. Windholz et al (1983) The Merck Index, 10th Edition, pp. 447–448.

*Primary Examiner*—Raymond J. Henley, Jr.

[57] ABSTRACT

A pharmaceutical composition for treating inflammatory diseases, comprising (A) an effective amount of hyaluronic acid or its salt, and (B) an effective amount of an anti-inflammatory agent. The composition exhibits a synergistic therapeutic effect on inflammations and is useful for treating inflammatory diseases, particularly diseases of joint with inflammation.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 21–35:

In a preferable embodiment of the present invention, hyaluronic acid or its salt is used in the form of a solution wherein it is dissolved in water or an aqueous solvent in such a concentration that the solution shows spinnability. An aqueous solution of hyaluronic acid or its salt which shows suitable spinnability has a viscosity of about 500 to 2,000 cps at [300°] *30°* C. In the case of sodium hyaluronate having a molecular weight of $8 \times 10^5$, a concentration of not less than 0.5% (w/v %, hereinafter the same), preferably 0.8 to 1.2%, is required to obtain such a suitable spinnability. A lower concentration (lower than 0.5%) is adoptable with increasing molecular weight of sodium hyaluronate and a higher concentration (more than 0.5%) is required with decreasing molecular weight of sodium hyaluronate.

AS A RESULT OF REEXAMINATION, IT HAS BEEN DETERMINED THAT:

Claims 1–5, 7 and 8 are cancelled.

Claim 6 is determined to be patentable as amended.

New claims 9–13 and 14 are added and determined to be patentable.

6. The composition of claim [1] *9*, wherein the nonsteroidal anti-inflammatory agent is diclofenac.

*9. A pharmaceutical composition for treating inflammatory diseases comprising an effective amount of a combination of (A) hyaluronic acid or a salt thereof and (B) a nonsteroidal anti-inflammatory agent for treating inflammatory diseases selected from the group consisting of a compound having formula (I):*

*wherein $R^1$ is a group selected from the group consisting of groups having formulas (II) and (III):*

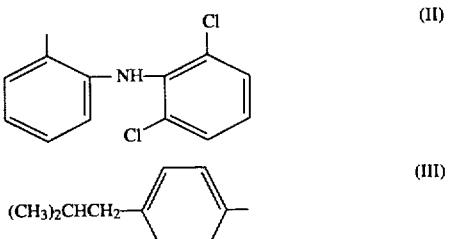

*and $R^2$ is H provided that $R^1$ is group II, or $R^2$ is —$CH_3$ provided that $R^1$ is group III; and a salt thereof.*

*10. The composition of claim 9, which is in a preparation form suitable for administration into an articular cavity.*

*11. The composition of claim 9, wherein the nonsteroidal anti-inflammatory agent is ibuprofen.*

*12. The composition of claim 9, wherein the ingredient (A) has a molecular weight from $4 \times 10^5$ to $3 \times 10^6$.*

*13. The composition of claim 9, wherein the ingredients (A) and (B) are present in a ratio of the hyaluronic acid or a salt thereof to the anti-inflammatory agent from 1:0.03 to 2 by weight.*

*14. The composition of claim 9, wherein the ingredients (A) and (B) are present in a ratio of the hyaluronic acid or a salt thereof to the anti-inflammatory agent from 1:0.1 to 1 by weight.*

\* \* \* \* \*